United States Patent [19]

Tabord

[11] Patent Number: 4,699,791

[45] Date of Patent: Oct. 13, 1987

[54] ANTISEPTIC PRODUCT AND A METHOD OF MANUFACTURE OF THE SAID PRODUCT

[76] Inventor: Jacques-Ami Tabord, Route de Féchy, 1165 Allaman, Switzerland

[21] Appl. No.: 772,867

[22] Filed: Sep. 5, 1985

[30] Foreign Application Priority Data

Sep. 17, 1984 [CH] Switzerland .................... 4445/84

[51] Int. Cl.$^4$ ............................................. A61K 35/78
[52] U.S. Cl. ................................................. 424/195.1
[58] Field of Search ...................................... 424/195.1

[56] References Cited

U.S. PATENT DOCUMENTS 3,812,272  5/1974  Linville ............................... 426/592
4,382,886  5/1983  Sosnowski ........................... 260/107

FOREIGN PATENT DOCUMENTS 1101118  3/1961  Fed. Rep. of Germany .

OTHER PUBLICATIONS

Chem. Abst., 94:145378e, 1981.
Chem. Abst., 98:95512d, 1983.

*Primary Examiner*—J. R. Brown
*Assistant Examiner*—John W. Rollins, Jr.
*Attorney, Agent, or Firm*—Robert E. Burns; Emmanuel J. Lobato

[57] ABSTRACT

The antiseptic product consists essentially of extracts of wine vinegar and honey. It may in addition advantageously contain extract of propolis. By the addition of specific natural ingredients one obtains antiseptic lotions, antiseptic tinctures, antiseptic handkerchiefs, and antiseptic shampoos or liquid soap and creams.

7 Claims, No Drawings

ANTISEPTIC PRODUCT AND A METHOD OF MANUFACTURE OF THE SAID PRODUCT

The object of the present invention is an antiseptic product based on natural raw materials.

There does not exist on the market today any antiseptic based on natural raw materials, with the exception of tincture of propolis administered principally by mouth.

The aim of the invention is to realize an antiseptic product based on natural raw materials which are non-toxic and are capable of being employed in various forms and in a very broad manner.

The antiseptic product in accordance with the invention is characterized in that it consists essentially of extract of wine vinegar and honey.

It has already been proposed to mix in equal volumes honey and vinegar diluted by water, in order to produce an additive for alcoholic drinks with the aim of neutralizing the odour of alcohol on the breath of the consumer (U.S. Pat. No. 3,812,272). It has likewise been proposed to employ a mixture containing honey and an edible acid such as vinegar for the preservation of fruit and vegetables (DE-A-1.101.118).

Furthermore the antiseptic properties of wine vinegar and honey are certainly known but extracts from them mixed in the given proportions offer a powerful synergy in their antiseptic effect. Laboratory tests upon animals and humans have confirmed a powerful bactericide, tuberculicide and fungicide effect.

As far as possible it is judicious to add to the mixture extract of propolis.

By adding suitable ingredients such as glycerine, flavourings, natural colourants, surfactants, emulsifiers and vegetable oils, it is possible to produce antiseptic products which appear in various forms such as antiseptic lotions, antiseptic tincture, preoperative antiseptic tincture, antiseptic handkerchiefs, and antiseptic shampoos as liquid soap and creams.

In the case of antiseptic lotions, tinctures and handkerchiefs, the afore-mentioned effects are already recognizable at the end of 30 seconds. For the antiseptic shampoos and cream a bactericide and fungicide effect has been found, which manifests itself after a length of time from 30 seconds to 8 minutes. Propolis has in addition a curative effect.

The object of the invention is likewise a method of manufacture of the antiseptic product, according to which the wine vinegar and the honey are extracted by filtration, the proportion of wine vinegar to honey being 30:1.

The antiseptic product and its method of manufacture are illustrated below by means of examples.

EXAMPLE I

Wine vinegar and honey are extracted at ambient temperature in 70° ethyl alcohol for one hour. The proportion of wine vinegar to honey should be 30:1. By filtration a clear alcohol extract is obtained.

A 10% tincture of propolis is prepared by extraction at ambient temperature in 70° ethyl alcohol and the tincture of propolis obtained is added to the extract of wine vinegar and honey.

It will be recalled here that ethyl alcohol or ethanol is a natural product the antiseptic properties of which have long been known.

The solution should contain 20 to 50 g of acetic acid and 0.50 to 1.00 g of propolis per liter.

Specific ingredients are then added, such as glycerine, perfumes, colourants, etc.

The final solution should be clear or very slightly opalescent.

EXAMPLE II

Wine vinegar and honey are extracted as in Example I.

The clear alcohol extract of wine vinegar and honey is diluted in 70° ethyl alcohol, so that the solution contains 20 to 50 g of acetic acid per liter.

The specific ingredients are then added, such as glycerine, perfumes, colourants, etc. for each of the preparations.

The final solutions should be clear or very slightly opalescent.

EXAMPLE III

The honey is made to dissolve entirely in the wine vinegar at ambient temperature. The proportion of honey to vinegar should be 1:30 and the total mixture should contain about 5% of acetic acid.

By filtration a clear extract is obtained which is employed for the preparation of antiseptic shampoos or liquid soap and creams.

For this purpose distilled water is added and other specific ingredients such as surfactants, emulsifiers, vegetable oils, perfumes, etc., the concentration of acetic acid being adapted in order to be from 50 to 75 g/kg in the preparations.

Into the mixture thus prepared is added purified extract of propolis, so that its content is from 1.0 to 2.0 g/kg expressed as of a dry substance.

What I claim is:

1. An antiseptic product for external use consisting essentially of 70° ethyl alcohol extract of wine vinegar and honey, the proportion of wine vinegar to honey being of the order of 30:1, wherein the extract of wine vinegar and honey is diluted in 70° ethyl alcohol to produce a product containing 20 g to 50 g of acetic acid per liter.

2. An antiseptic product as claimed in claim 1, wherein the product further contains 10% tincture of propolis in the amount of the order of 0.5 g to 1 g of propolis per liter of product.

3. An antiseptic product as claimed in claim 2, wherein it consists in the addition of at least one other ingredient selected from the group consisting of glycerine, perfume, colorant, surfactants, emulsifier and vegetable oil.

4. A method of manufacturing of an antiseptic product for external use which comprises blending wine vinegar and honey in the proportion of the order of 30:1, extracting said wine vinegar and honey at ambient temperature in 70° ethyl alcohol, filtering the extract thus obtained, preparing a 10% tincture of propolis by extraction at ambient temperature in 70° ethyl alcohol and adding said tincture of propolis to said extract of wine vinegar and honey with the proportion of 20 g to 50 g of acetic acid and 0.5 g to 1 g of propolis per liter of product.

5. A method of manufacturing according to claim 4, further comprising the step of adding to said product at least one ingredient selected from the group consisting of glycerine, perfume, colorant, surfactant, emulsifier and vegetable oil.

6. A method of manufacture of an antiseptic product for external use which comprises dissolving honey in wine vinegar at ambient temperature in the proportion of the order of 1:30 and adding distilled water to produce an extract containing about 5% of acetic acid, filtering said extract, preparing a tincture of propolis by extraction at ambient temperature in 70% ethyl alcohol and adding said tincture of propolis to said extract of wine vinegar and honey in the proportion of about 1 g to 2 g of propolis per kilogram of product.

7. A method of manufacture according to claim 6 further comprising adding at least one ingredient selected from the group consisting of glycerine, perfume, colorant, surfactant, emulsifier and vegetable oil.

* * * * *